United States Patent [19]

Speer et al.

[11] Patent Number: 4,739,087
[45] Date of Patent: Apr. 19, 1988

[54] ANTINEOPLASTIC PLATINUM COMPLEXES

[75] Inventors: Robert J. Speer, Richardson; David P. Stewart, Fort Worth, both of Tex.

[73] Assignee: Bristol-Myers Company, New York, N.Y.

[21] Appl. No.: 690,436

[22] Filed: Jan. 10, 1985

[51] Int. Cl.$^4$ .......................................... C07F 15/00
[52] U.S. Cl. ................................................ 556/137
[58] Field of Search ..................... 260/429 R; 556/137

[56] References Cited

U.S. PATENT DOCUMENTS

| 4,115,418 | 9/1978 | Gale et al. | 260/429 R |
|---|---|---|---|
| 4,169,846 | 10/1979 | Kidani et al. | 260/429 R |
| 4,256,652 | 3/1981 | Kidani et al. | 260/429 R |
| 4,284,579 | 8/1981 | Meischen et al. | 260/429 R |
| 4,359,425 | 11/1982 | Totani et al. | 260/429 R |
| 4,562,275 | 12/1985 | Speer et al. | 556/137 X |
| 4,661,516 | 4/1987 | Brown et al. | 514/492 |

FOREIGN PATENT DOCUMENTS

| 2003468 | 3/1979 | United Kingdom . |
|---|---|---|
| 2024823A | 1/1980 | United Kingdom . |
| 2093845 | 9/1982 | United Kingdom . |

OTHER PUBLICATIONS

*Nature* 222, Platinum Compounds: A New Class of Potent Antitumor Agents, B. Rosenberg et al., pp. 385–386, 1969.
*Proc. Am. Assoc. Cancer Res.* 13:20, cis-Platinous Diammino Dichloride (PDD) Therapy of Various Malignant Diseases, J. Hill et al., 1972.
*Bioinorg. Chem.* 2: Platinum (II) Complexes, M. J. Cleare et al., 187–210, 1973.
*Chem. Biol. Interact.* 5, New Platinum Complexes with Antitumor Activity, Connors et al, 415–424, 1972.
*J. Inorg. Biochem.* 11: Synthesis and Activity Against Mouse Leukemia L1210, Hall et al., 139–149, 1979.
*Cancer Treatment Reports* 61 (8): Preparation and Antitumor Evaluation of Water–Soluble Derivatives of Dichloro (1,2–Diaminocyclohexane), P. Schwartz et al., 1519–1525, 1977.
*J. Med. Chem.* 21 (12), Y. Kidani et al., 1315–1318, 1978.
*J. Clin. Hematol. Oncol.* 7 (1): Analogs of Sulfato 1,2–Diaminocyclohexane Platinum (II) (SHP) II, Modifications Other Than Leaving Ligand, 231–240, 1977.
*J. Clin. Hematol. Oncol.* 7 (1) Analogs of Sulfato 12,–Diaminocyclohexane Platinum (II), Modifications in Leaving Ligand. 220–228., 1977.
*Gann* 67: Y. Kidani et al. Examination of Antitumor Activities of Platinum Complexes of 1,2–Diaminocyclohexane Isomers and Their Related Complexes, 921–922, 1976.
*J. Clin. Hematol. Oncol.* 8 (2): Antitumor Activity of Platinum Complexes of 1,2–Diaminocyclohexane Isomers, 44–50, 1978, Speer et al.
*J. Clin. Hematol. Oncol.* 9 (1): Glen R. Gale et al., Preliminary Studies of 4-Carboxyphthalato (1,2-Diaminocyclohexane) Platinum (II) Antitumor Activity and Effects on Macromolecular Synthesis, 174, 1979.
*J. Clin. Hematol. Oncol.* 9 (3): 217–234, 1979.

Primary Examiner—Paul F. Shaver
Attorney, Agent, or Firm—David M. Morse

[57] ABSTRACT

Novel platinum(II) complexes of 1,2-diaminocyclohexane, 2,2'-bipiperidine, 1,2-diamino-2,4-dimethylpentane, 1,2-diaminocyclooctane, 3,4-diamino-2,5-dimethylhexane and 1-aminomethylcyclooctylamine are provided: such complexes are of use in inhibiting the growth of certain mammalian tumors.

11 Claims, No Drawings

ANTINEOPLASTIC PLATINUM COMPLEXES

BACKGROUND OF THE INVENTION

1. Field of the Invention

This invention concerns certain novel platinum complexes having antineoplastic activity. More explicitly, it relates to novel antitumor platinum complexes of 1,2-diaminocyclohexane, 2,2'-bipiperidyl, 1,2-diamino-2,4-dimethylpentane, 1,2-diaminocyclooctane, 3,4-diamino-2,5-dimethylhexane, and 1-aminomethylcyclooctylamine and a variety of more labile ligands.

2. Description of the Prior Art

Rosenberg et al first reported that certain platinum complexes possess antitumor activity against a variety of murine malignancies [B. Rosenberg, L. Van Camp, J. E. Trosko, and V. H. Mansour. Platinum Compounds: A New Class of Potent Antitumor Agents. *Nature* 222:385–386, 1969]. Hill et al first utilized the platinum complex, cis-dichlorodiammine platinum(II), cisplatin, for the treatment of human cancer patients [J. M. Hill, E. Loeb, R. J. Speer, A. MacLellan, and N. O. Hill. cis-Platinous Diammino Dichloride (PDD) Therapy of Various Malignant Diseases. *Proc. Am. Assoc. Cancer Res.* 13:20, 1972]. A very informative survey of platinum complexes as antitumor agents was provided by Cleare and Hoeschele [M. J. Cleare and J. D. Hoeschele. Studies on the Antitumor Activity of Group VIII Transition Metal Complexes. Part I. Platinum(II) Complexes. *Bioinorg. Chem.* 2:187–210, 1973]. These authors were the first to make and test complexes of 1,2-diaminocyclohexane as well as a variety of more labile ligands, especially mono- and di-carboxylates. Connors et al [T. A. Connors, M. Jones, W. C. Ross, P. D. Braddock, A. R. Kohkhar, and M. L. Tobe. New Platinum Complexes with Antitumor Activity. *Chem.-Biol. Interact.* 5:415–424, 1972], and Hall et al [Larry M. Hall, Robert J. Speer, Helen J. Ridgway, and S. J. Norton. Unsymmetrical C-Substituted Ethylenediamine Platinum Coordination Complexes: Synthesis and Activity Against Mouse Leukemia L1210. *J. Inorg. Biochem.* 11:139–149, 1979] have also contributed to our understanding of the value of alicyclic diamines in the preparation of platinum antitumor complexes. Other literature of significance includes: [Paul Schwartz, Sandra J. Meischen, Glen R. Gale, Loretta M. Atkins, Alayne B. Smith, and Ernest M. Walker, Jr. Preparation and Antitumor Evaluation of Water-Soluble Derivatives of Dichloro(1,2-Diaminocyclohexane) Platinum(II). *Cancer Treatment Reports* 61 (8): 1519–1525, 1977], [U.S. Pat. No. 4,169,846], [Yoshinori Kidani and Kenji Inagaki. Antitumor Activity of 1,2-Diaminocyclohexane-Platinum Complexes Against Sarcoma-180 Ascites Form. *J. Med. Chem.* 21(12):1315–1318, 1978], [Larry M. Hall, Robert J. Speer, Helen J. Ridgway, David P. Stewart, Andrew D. Newman, and Joseph M. Hill. Analogs of Sulfato 1,2-Diaminocyclohexane Platinum-(II) (SHP) II. Modifications Other Than Leaving Ligand. *J. Clin. Hematol. Oncol.* 7(1):231–240,1977], [U.K. Patent Application No. 2,003,468A], [Helen J. Ridgway, Robert J. Speer, Larry M. Hall, David P. Stewart, Andrew D. Newman, and Joseph M. Hill. Analogs of Sulfato 1,2-Diaminocyclohexane Platinum(II). I. Modifications in Leaving Ligand. *J. Clin. Hematol. Oncol.* 7(1):220–228, 1977], [Yoshinori Kidani, Kenji Inagaki, and Shigeru Tsukagoshi. Examination of Antitumor Activities of Platinum Complexes of 1,2-Diaminocyclohexane Isomers and Their Related Complexes. *Gann* 67:921–922, 1976], [Robert J. Speer, Larry M. Hall, David P. Stewart, Helen J. Ridgway, Joseph M. Hill, and Yoshinori Kidani. Antitumor Activity of Platinum Complexes of 1,2-Diaminocyclohexane Isomers. *J. Clin. Hematol. Oncol.* 8(2):44–50, 1978], [D. P. Stewart, R. J. Speer, H. J. Ridgway, and J. M. Hill. Antitumor Activity of Platinum Complexes of trans-3,4-Diamino-2,5-Dimethylhexane Against Mouse Leukemia L1210. *J. Clin. Hematol. Oncol.* 9(1):174,1979], [Glen R. Gale, Alayne B. Smith, and Paul Schwartz. Preliminary Studies of 4-Carboxyphthalato (1,2-Diaminocyclohexane) Platinum(II): Antitumor Activity and Effects on Macromolecular Synthesis. *J. Clin. Hematol. Oncol.* 9(3):217–234, 1979], [U.S. Pat. No. 4,115,418], [U.S. Pat. No. 4,256,652], [U.S. Pat. No. 4,284,579], [U.S. Pat. No. 4,359,425], [European Patent Application No. 55,300], [U.K. Patent Application No. 2,093,845], [U.K. Patent Application No. 2,024,823A], and others.

It is evident from the above that a large number of platinum complexes has been reported as having some antitumor activity; however, there remains a need for new platinum antineoplastic complexes which have more advantageous properties, e.g., greater solubility in intravenous fluids, improved stability when dissolved in intravenous fluids, greater antitumor potency, broader spectrum of activity against human malignancies, and less toxicity to patient's kidney, inner ear, gut, bone marrow, etc. It is especially desirable that such new antitumor platinum complexes possess significant advantages over cisplatin, the only platinum complex presently being marketed as an anticancer agent.

SUMMARY OF THE INVENTION

The present invention provides in one aspect certain novel platinum complexes of the general formula

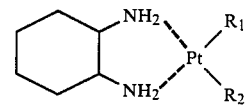

wherein the stereoisomerism of 1,2-diaminocyclohexane is cis-, trans(+)- or trans(−)- and $R_1$ and $R_2$ are both 4-hydroxyphenylsulfonato-, perfluorooctanoato-, or pentafluoroproprionato-, with the following structures:

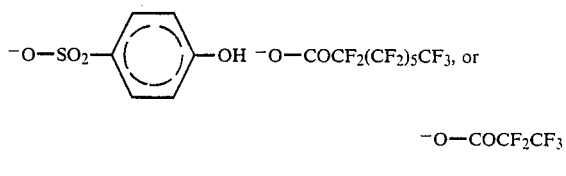

or where $R_1$ and $R_2$, when taken together, represent a group of the type N-2-hydroxyethyliminodiacetato-, 2-sulfobenzoato-, 1,2-benzenedisulfonato-, inosine monophosphato-, 4-aminophenylarsonato-, 3-ketoglutarato-, ribose-5-phosphato-, 2-aminoethylphosphato-, n-hexylphosphonato-, pyridoxal phosphato-, 2-hydroxyethane-1,1-diphosphonato-, tungstato-, or arsonacetatodivalent, chelating ligands. These structures are:

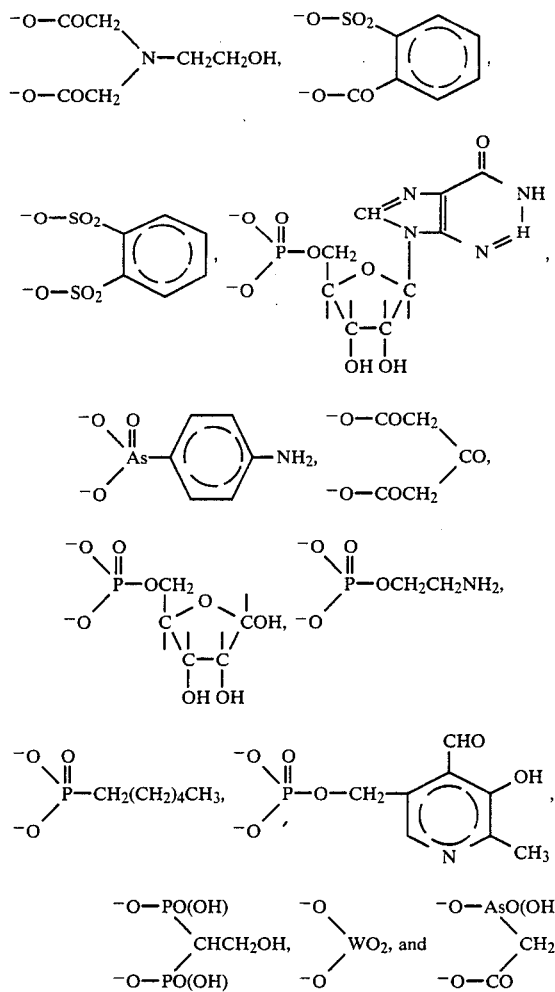

Another aspect of the present invention provides platinum complexes of the general formula

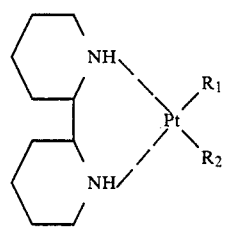

wherein $R_1$ and $R_2$ are both $-OH$.

In yet another aspect this present invention provides platinum complexes derived from 1,2-diamino-2,4-dimethylpentane of the general type

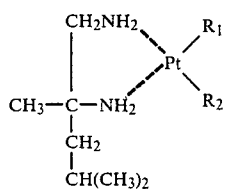

wherein $R_1$ and $R_2$ are both

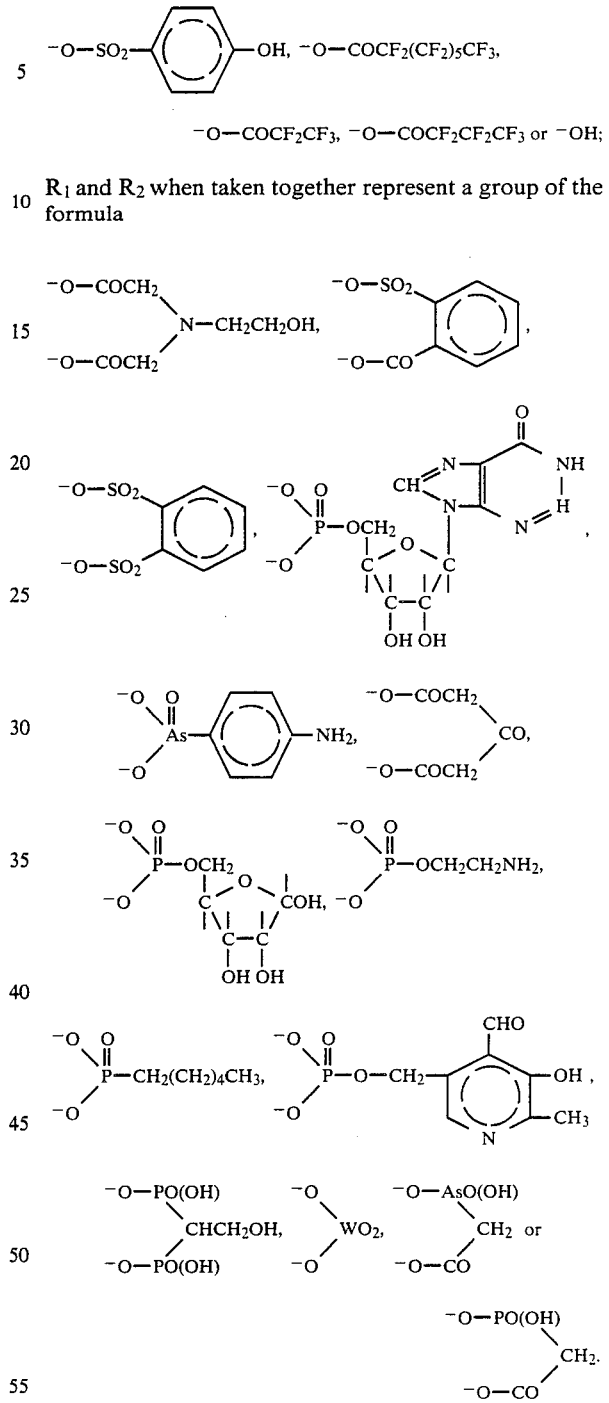

$R_1$ and $R_2$ when taken together represent a group of the formula

This present invention also provides certain unique platinum complexes derived from 1,2-diaminocyclooctane of the general structure

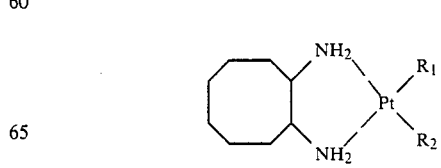

wherein $R_1$ and $R_2$ are both

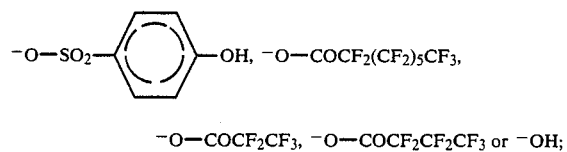

or $R_1$ and $R_2$ when taken together represent a group of the formula

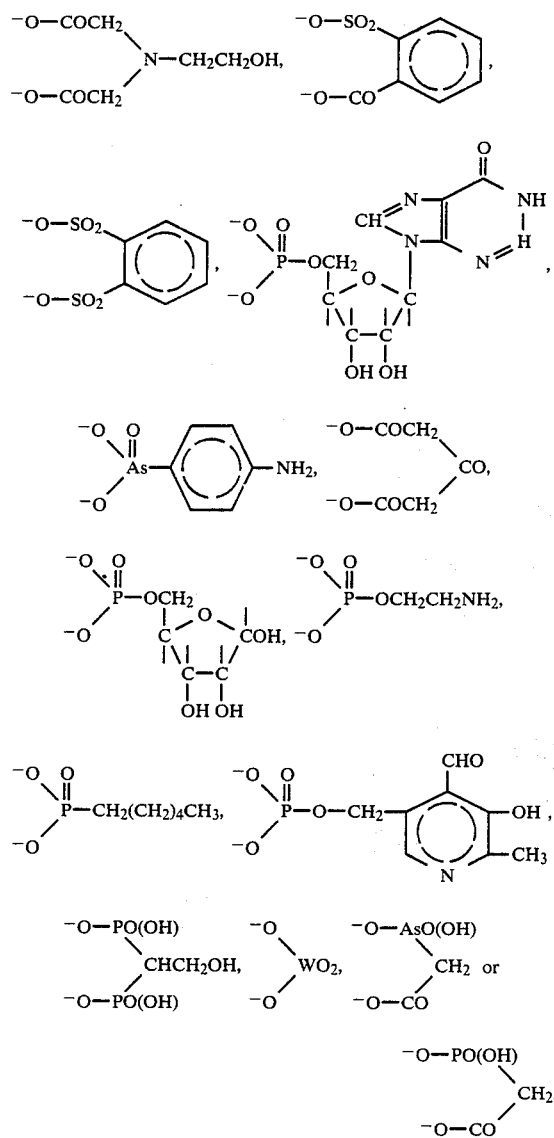

This present invention also provides platinum complexes incorporating 3,4-diamino-2,5-dimethylhexane as a non-leaving ligand of the general formula $$(CH_3)_2CHCH-NH_2 \quad R_1$$
$$\phantom{(CH_3)_2CHCH-NH_2}\backslash Pt$$
$$(CH_3)_2CHCH-NH_2 \quad R_2$$

wherein $R_1$ and $R_2$ are both

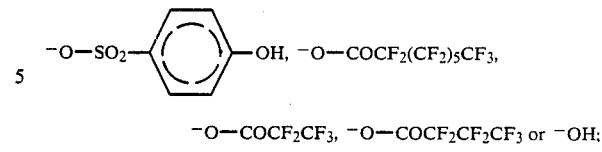

or $R_1$ and $R_2$ when taken together represent a group of the formula

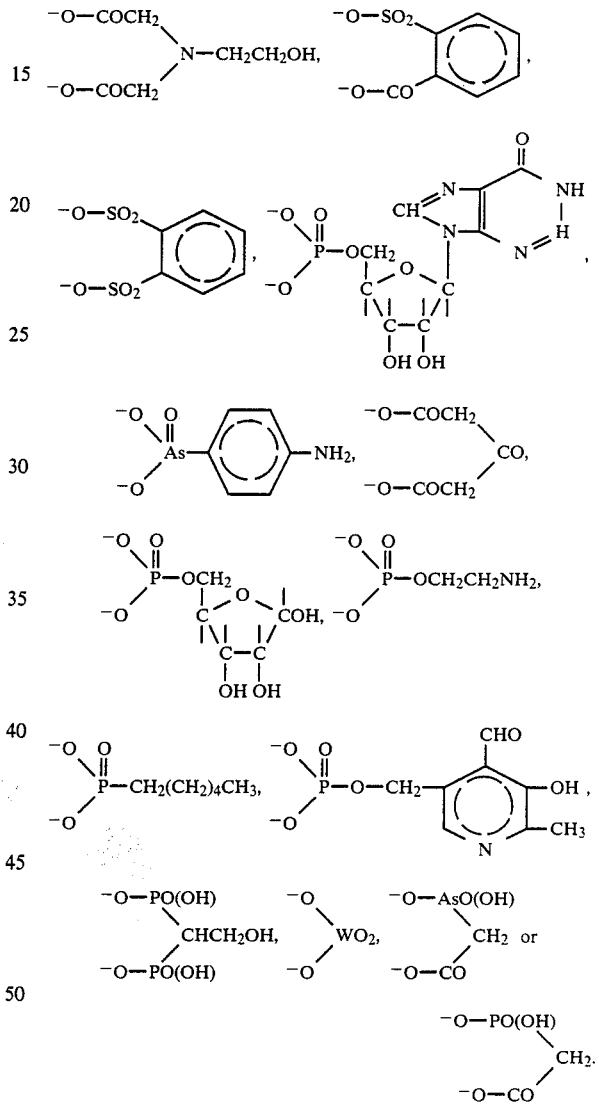

In yet another aspect this present invention provides platinum complexes derived from 1-aminomethylcyclooctylamine of the type

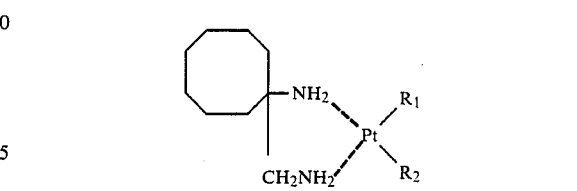

wherein $R_1$ and $R_2$ are both

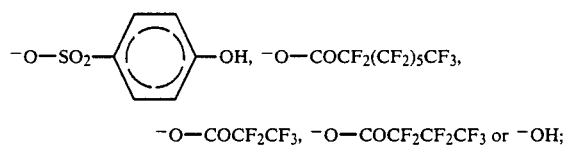

or $R_1$ and $R_2$ when taken together represent a group of the formula

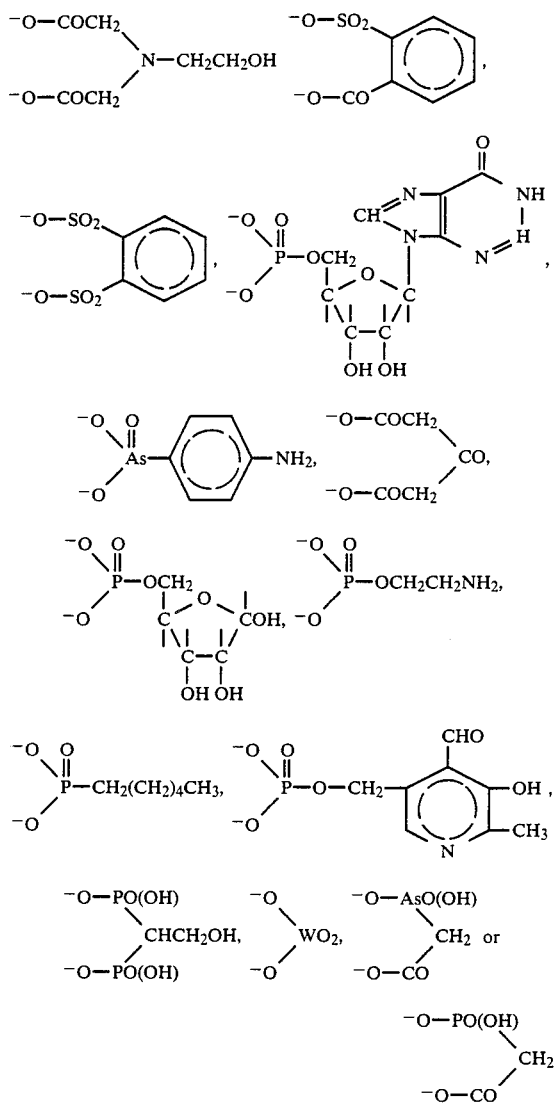

From the above, it is evident that this present invention provides platinum complexes incorporating 6 substituted amines and in their stereoisomeric forms as non-leaving ligands and 19 varied, novel, labile, leaving ligands combined in new and unique associations. They thus achieve unique and desirable properties, vis-a-vis, solubilities, stabilities, activity against experimental murine malignancies, and minimal toxicity.

DETAILED DESCRIPTION OF THE INVENTION

In general, the complexes of this present invention are prepared from the corresponding dichloro platinum complexes which have been previously described in the scientific literature. Synthesis of the dichloro complexes of 1-aminomethylcyclooctylamine and 1,2-diamino-2,4-dimethylpentane is described, for example, in J. Inorg. Biochem. 11: 139–149, 1979. The synthesis of cis-, trans(+)-, and trans(−)-dichloro 1,2-diaminocyclohexane platinum(II) is disclosed in U.S. Pat. No. 4,169,846. As noted above, any of the cis-, trans(+)-, trans(−)-isomers of the cis-dichloro 1,2-diaminocyclohexane platinum(II) or mixtures of isomers, can be employed as the starting material for synthesis. The novel complexes of 1,2-diaminocyclohexane herein disclosed are preferably prepared from the trans(−)- starting material, since the resulting biological activity of the end-products is superior to those derived from other isomers or an isomeric mixture.

Complexes of the present invention are synthesized from the corresponding dichloro platinum complexes by synthetic methods familiar to those skilled in the art and prior scientific literature. In one suitable procedure, for example, the appropriate dichloro complex is allowed to react with the silver salt of the desired ligand. Typically 1 mmol (or some multiple thereof) of the dichloro complex is treated with 0.95 mmol of the appropriate disilver salt in water. Silver chloride precipitates and is removed by filtration. The resulting complex is isolated from the filtrate by vacuum evaporation at low temperature or by precipitation with an excess of an organic solvent (acetone or ethanol) in the cold. The product is washed with an excess of organic solvent in which the complex itself is substantially insoluble and then dried in vacuo in the dark over anhydrous silica gel or other dessicant. This procedure is illustrated in examples 4, 5, 7, and 17 below. Another satisfactory synthetic procedure involves the preliminary formation in situ of the dinitrato platinum complex and the subsequent treatment of this intermediate with an alkali metal salt or the free acid of the desired ligand. Typically about 1 mmol (or some multiple thereof) of the dichloro complex is treated with 1.95 mmol of silver nitrate in water in the dark at 20°–70° C., for 1–24 hours. Most generally the reaction mixture is agitated at room temperature for 10–16 hours, chilled to 0°–4° C., and filtered. To the filtrate is added an aqueous solution of 1 mmol of a bidentate (or 2 mmol of a monodentate) ligand (free acid or alkali metal salt thereof). When the resulting complex is sufficiently insoluble in water, the product precipitates and may be removed by filtration. In some instances, warming at 50°–80° C. and subsequent cooling to 0°–4° C. hasten formation and recovery of the complex. Such synthetic methodology is illustrated in examples 12, 15, and 21 below.

An especially preferred procedure involves conversion of the dichloro complex to the dihydroxy intermediate followed by subsequent reaction with the desired ligand. Typically an aqueous solution of dichloro platinum complex is allowed to react with silver sulfate ($Ag_2SO_4$) with stirring in the dark at room temperature for 12–24 hours. The resulting solution is filtered. (Completion of the reaction can be assumed when a drop of saline solution produces no precipitate of silver chloride when added to a drop of the filtrate.) At this point, the reaction vessel contains a solution of the sulfato platinum complex which is utilized without isolation. The reaction mixture is filtered, and barium hydroxide is added to the filtrate in stoichiometric amount to produce insoluble barium sulfate. This is generally achieved by an additional period of agitation in the dark at room temperature for 2-24 hours. Filtration yields a solution of the corresponding dihydroxy platinum complex as a versatile synthetic intermediate. The solution is then allowed to interact with the desired ligand (free acid form) to yield the corresponding end-product. If essentially insoluble in water, the end-product can be obtained by filtration. If, however, the resulting complex is appreciably soluble in water, it may be recovered by evaporation at low temperature in vacuo or by addition of an excess of acetone, ethanol, or other solvent. This versatile procedure is illustrated in examples 1, 2, 3, 8, 9, 10, 11, 13, 14, 16, 18, 19, and 20.

Product complexes obtained according to the present invention generally require no further purification. However, if necessary, they can be purified by conventional procedure, e.g., by dissolution in a suitable solvent such as water, dimethyl formamide, ethanol, etc., and precipitation by slow addition of a large excess of a solvent in which the desired complex is essentially insoluble, e.g., acetone, ethanol, methanol, diethyl ether, etc. Products can be harvested by filtration, washed with solvents of the latter type, and dried over anhydrous silica gel or other dessicant in vacuo in the dark.

The identify and purity of these platinum complexes are verified by IR spectroscopy, thin layer chromatography, elemental analysis, and other conventional methods familiar to those skilled in the art.

BIOLOGICAL PROPERTIES OF COMPLEXES

The antitumor activities of the platinum complexes provided by the present invention have been evaluated using the ascites form of L1210 leukemia in the $BDF_1$ mouse. For certain of these complexes, antitumor activity was also tested in vitro against L1210 according to the method of Hamburger and Salmon. [A. Hamburger and S. E. Salmon. Primary Bioassay of Human Tumor Stem Cells. *Science* 197: 461-462, 1977] and [Helen Ridgway, David P. Stewart, Nancy Michaelis, Michael J. Guthrie, and Robert J. Speer. Successful Screening of Platinum Complexes as Potential Antitumor Agents with an L1210 Clonogenic Assay. *J. Clin. Hematol. Oncol.* 14 (1): 1-7, 1984.] To a very limited extent certain of these complexes have been tested for their antitumor activity against the advanced solid B16 melanoma in mice [R. J. Speer, C. J. Storey, L. M. Hall, and H. J. Ridgway. Relative Therapeutic Efficacy of Platinum Complexes Against the Advanced B16 Melanoma in mice. *J. Clin. Hematol. Oncol.* 11 (2): 47-53, 1981.] The results of antitumor testing against the murine leukemia L1210 are presented below. In general, it should be noted that this testing method entails the i.p. transplantation of $10^4$ L1210 cells to $BDF_1$ mice (18-25 g) on day 0, administration of various doses of each complex in an appropriate vehicle as a single i.p. injection on day 3, and tabulation of results until 200% increased life span (%ILS) as compared to untreated tumor-bearing control mice. Experiments were arbitrarily terminated at 200%ILS, and survivors at this point are considered "cured", since tumor deaths beyond this time are very rare. Any result $\geq 25\%$ILS is regarded as significant antitumor activity. These methods have been described in greater detail by the inventors in the literature listed above. Explanation of certain abbreviations: $LD_{50}$ is that single dose of complex which killed 50% of test animals. $ID_{99.9}$ is that single dose of complex which killed 99.9% of malignant L1210 cells and corresponds to 48%ILS. Figure of merit=$(LD_{50} \times$ Best %ILS at any dose of complex$)/(ID_{99.9} \times 100)$. For comparison, it should be noted that in this test system, cisplatin has an $LD_{50}$ of 14.0 mg/kg, $ID_{99.9}=4.5$ mg/kg, Best-%ILS=106, figure of merit=3.3. Comparison of the figures of merit for the present invention with that of cisplatin provides a particularly useful assessment of these new complexes' potential value in man, since this parameter incorporates both antitumor potency and toxicity data. Thus, the higher the figure of merit, the better the therapeutic index of the platinum complex, vis-a-vis, the wider the spread between toxic dose and efficacious dose.

As clearly shown by the antitumor activity data for representative examples below, the platinum compounds of the present invention exhibit significant inhibitory activity against murine leukemia L1210. According to one aspect of the present invention, therefore, a method is provided for therapeutically treating a mammalian host affected by a malignant tumor which comprises administering to said host an effective tumor-inhibiting dose of a platinum complex of the present invention, i.e., the product described as illustrative in examples 1-21 below.

According to another aspect, a pharmaceutical composition is provided which comprises a tumor-inhibiting amount of a complex of the present invention in combination with a pharmaceutically acceptable carrier, diluent, or vehicle.

The product complexes of this present invention are preferably administered in the usual manner as other antitumor platinum complexes known in the art, e.g., cisplatin. Preparations for parenteral administration include stable aqueous or non-aqueous solutions, suspensions or emulsions. They also may be manufactured in the form of sterile solid compositions which can be dissolved in sterile water, physiologic saline, 5% dextrose in water, or some other sterile injectable medium prior to their administration.

It will be appreciated that the actual preferred dosage amounts will vary according to the specific platinum complex being used, the particular composition formulated, the mode of application, and the particular situs, host, and disease being treated. In general, the compounds are injected intraperitoneally, subcutaneously, or locally. Many factors that modify the action of the drug will be taken into account by those skilled in the art, for example, age, body weight, sex, diet, time of administration, route of administration, rate of excretion, condition of the host, drug combinations, drug hyper-sensitivities, and severity of the disease. Administration may be continuous or periodic within the maximum tolerated dose. Optimal application rate for a given set of conditions can be ascertained by those skilled in the art using conventional principles and medical practice.

Illustrative methods for preparing complexes provided by the present invention are described below. These examples, however, are not meant to limit the scope of the invention to the specific procedures employed. Volume ratios used to describe solvent systems are volume/volume.

EXAMPLE 1

Preparation of N-2-Hydroxyethyliminodiacetato trans(−)-1,2-Diaminocyclohexane Platinum(II)

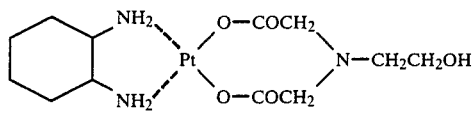

A mixture of cis-dichloro trans(−)-1,2-diaminocyclohexane platinum (II) (380 mg) and silver sulfate ($Ag_2SO_4$, 312 mg) in 25 ml water was stirred at room temperature in the dark for 24 hours. The resulting suspension was filtered (no silver was detectable in the filtrate), and barium hydroxide [$Ba(OH)_2.8H_2O$, 315 mg] was added to the filtrate and the stirring continued at room temperature in the dark for 24 hours. The reaction mixture was filtered to remove barium sulfate. To the filtrate was added N-2-hydroxyethyliminodiacetic acid (177 mg), and the mixture was stirred at 50° C. for 2 hours. During this interval, the reaction mixture turned from yellow to colorless. Reaction product was obtained by low temperature evaporation in vacuo. The solid was washed thoroughly with ethanol and dried under vacuum in the dark over anhydrous silica gel. Yield was 210 mg. The title complex was very soluble in water, in 5% dextrose in water (D5W), and in 1% sodium bicarbonate solution, but essentially insoluble in methanol, ethanol, and dimethyl formamide. No further purification was required. IR spectroscopy was compatible with the structure shown above. Homogeneity of the product was demonstrated by thin layer chromatography (TLC) on microcrystalline cellulose using n-butanol:acetic acid:water (12:3:5), the $R_f$ was 0.49, and in isopropanol:0.1N ammonium hydroxide (1:1), the $R_f$ was 0.58.

When tested for antitumor activity against leukemia L1210 in $BDF_1$ mice, the title complex demonstrateed: $ID_{99.9}=25$ mg/kg, $LD_{50}=125$ mg/kg, Best-%ILS=110, and figure of merit=5.

EXAMPLE 2

Synthesis of bis(4-Hydroxyphenylsulfonato) trans(−)-1,2-Diaminocyclohexane Platinum(II)

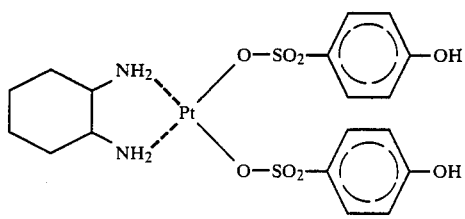

A mixture of cis-dichloro trans(−)-1,2-diaminocyclohexane platinum(II) (380 mg) and silver sulfate ($Ag_2SO_4$, 312 mg) in 25 ml water was stirred at room temperature in the dark for 24 hours. The resulting suspension was filtered (no silver was detectable in the filtrate), and barium hydroxide [$Ba(OH)_2.8H_2O$, 315 mg] was added to the filtrate and the stirring continued at room temperature in the dark for 24 hours. The reaction mixture was filtered to remove barium sulfate. 4-Hydroxybenzenesulfonic acid (348 mg) was added and the reaction mixture stirred at 50° C. for one hour. A purple precipitate separated from solution, was collected by filtration, and washed with water and with methanol. The product was dried in vacuo in the dark over anhydrous silica gel. Yield was 235 mg. This complex is soluble in dimethylformamide (DMF) and dimethylsulfoxide (DMSO) but essentially insoluble in water, methanol, ethanol, D5W, and 1% sodium carbonate solution. No further purification was required. The IR spectrum was consistent with the structure indicated above. The purity of this complex was established by the TLC systems noted in example 1; in n-butanol:acetic acid:water, $R_f=0.75$, and in isopropanol:0.1N ammonium hydroxide, the $R_f=0.65$.

When tested against the murine leukemia L1210, this complex showed: $ID_{99.9}=3$ mg/kg, $LD_{50}=50$ mg/kg, Best %ILS=100, and figure of merit=17.

EXAMPLE 3

Preparation of 2-Sulfobenzoato trans(−)-1,2-Diaminocyclohexane Platinum(II)

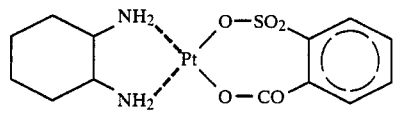

A mixture of cis-dichloro trans(−)-1,2-diaminocyclohexane platinum(II) (380 mg) and silver sulfate ($Ag_2SO_4$, 312 mg) in 25 ml water was stirred at room temperature in the dark for 24 hours. The resulting suspension was filtered (no silver was detectable in the filtrate), and barium hydroxide [$Ba(OH)_2.8H_2O$, 315 mg] was added to the filtrate and the stirring continued at room temperature in the dark for 24 hours. The reaction mixture was filtered to remove barium sulfate. o-Sulfobenzoic acid (200 mg) was added to the filtrate, and the reaction mixture was stirred and heated at 50° C. for 2 hours. A yellow precipitate formed, was removed by filtration, and was washed with water and methanol. The complex was dried in vacuo in the dark over anhydrous silica gel. Yield was 230 mg. No further purification was required. The product was slightly soluble in DMF and DMSO but was essentially insoluble in water, D5W, methanol, and ethanol. The IR spectrum was consistent for the structure indicated above. The purity of this complex was verified by TLC in n-butanol:acetic acid:water with an $R_f=0.92$ and in isopropanol:0.1N ammonium hydroxide where the $R_f$ was 0.88.

This complex showed significant inhibition of the L1210 leukemia in $BDF_1$ mice; the $ID_{99.9}$ was 4 mg/kg, the $LD_{50}$ was 60 mg/kg, the Best%ILS was 200, and the figure of merit was 30.

EXAMPLE 4

Preparation of 1,2-Benzenedisulfonato trans(−)-1,2-Diaminocyclohexane Platinum(II)

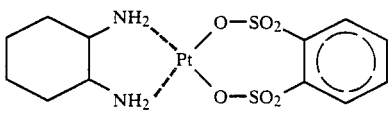

A mixture of cis-dichloro trans(−)-1,2-diaminocyclohexane platinum(II) (380 mg) and 452 mg of disilver o-benzenedisulfonate was suspended in 25 ml of water. This mixture was stirred at room temperature in the dark for 24 hours. The reaction mixture was filtered and the filtrate evaporated under vacuum. The crude solid was washed with methanol and dried in vacuo in the dark over anhydrous silica gel; the yield was 270 mg. It required no further purification. The title complex was soluble in water; however, it was essentially insoluble in methanol and ethanol. IR spectroscopy was compatible with the structure indicated above. The product was homogeneous as judged by TLC in n-butanol:acetic acid:water, $R_f=0.55$ and in isopropanol:0.1N ammonium hydroxide, $R_f=0.60$.

Antitumor testing with leukemia L1210 in BDF$_1$ mice revealed: $ID_{99.9}=2$ mg/kg, $LD_{50}=15$ mg/kg, Best%ILS=123, and figure of merit=9.

EXAMPLE 5

Preparation of (Inosine Monophosphato) trans(−)-1,2-Diaminocyclohexane Platinum(II)

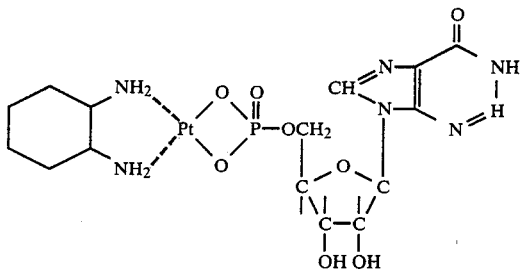

A mixture of cis-dichloro trans(−)-1,2-diaminocyclohexane platinum(II) (380 mg) and 562 mg of disilver inosine monophosphate was suspended in 25 ml of water. The reaction mixture was stirred in the dark at room temperature for 24 hours, filtered, and the filtrate evaporated to dryness in vacuo. The title complex was washed with methanol and dried in vacuo in the dark over anhydrous silica gel. Yield was 350 mg. No further purification of the product was necessary. IR spectroscopy was consistent for the indicated structure. TLC in n-butanol:acetic acid:water revealed a single product with an $R_f$ of 0.75 and in isopropanol:0.1N ammonium hydroxide an $R_f$ of 0.79.

Antitumor testing against L1210 leukemia showed a Best%ILS of 155 at a dose of 160 mg/kg, %ILS=100 at a dose of 40 mg/kg, and an ILS of 36% at a dose of 10 mg/kg. Several cures were observed in the course of this testing.

EXAMPLE 6

Synthesis of cis(Dihydroxy) 2,2'-Bipiperidyl Platinum(II)

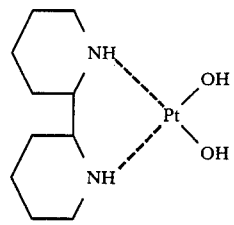

A mixture of cis-dichloro 2,2'-bipiperidyl platinum-(II) (432 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. The filtrate was evaporated to dryness in vacuo, and the resulting solid was dried in vacuo in the dark over anhydrous silica gel. The yield of product was 250 mg; it required no further purification. The title complex was soluble in water, D5W, and methanol, but it was essentially insoluble in DMF, dimethylacetamide (DMA), acetone, and chloroform. The IR spectrum was consistent with the structure shown above. The complex was pure, as judged by TLC in n-butanol:acetic acid:water, $R_f=0.87$, and in isopropanol:0.1N ammonium hydroxide, $R_f=0.85$.

The title complex showed antitumor activity against leukemia L1210: $ID_{99.9}=33$ mg/kg, $LD_{50}=150$ mg/kg, Best%ILS=100, and figure of merit=5.

EXAMPLE 7

Preparation of Tungstato trans(−)-1,2-Diaminocyclohexane Platinum(II)

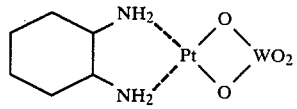

A mixture of cis-dichloro trans(−)-1,2-diaminocyclohexane platinum(II) (380 mg) and 454 mg of disilver tungstate was suspended in 25 ml of water. The reaction mixture was stirred at room temperature in the dark for 60 hours, filtered, and the filtrate evaporated in vacuo to dryness. The residue was washed with methanol and then dried in vacuo in the dark over anhydrous silica gel. The yield was 70 mg. The title complex was soluble in water and D5W but was insoluble in methanol, ethanol, and DMF. The IR spectrum was compatible with the structure shown above. The product required no further purification as was indicated by homogeneity in the TLC system n-butanol:acetic acid:water, $R_f=0.74$, and in isopropanol:0.1N ammonium hydroxide, $R_f=0.50$.

This complex showed significant antitumor activity against mouse leukemia L1210, e.g., $ID_{99.9}=3$ mg/kg, $LD_{50}=28$ mg/kg, Best%ILS=145, and figure of merit=11.

EXAMPLE 8

Formation of 4-Aminophenylarsonato trans(−)-1,2-Diaminocyclohexane Platinum(II)

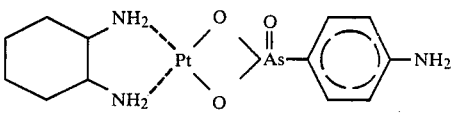

A mixture of cis-dichloro trans(−)-1,2-diaminocyclohexane platinum(II) (380 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. To the filtrate was added 4-aminophenyl-arsonic acid (217 mg), and the reaction mixture was stirred and heated 2 hours at 60° C. in the dark. During this reaction the solution turned from light yellow to dark brown, but no precipitate was formed. Product was obtained by evaporation of the reaction mixture to dryness in vacuo. After the product was washed thoroughly with methanol, it was dried in vacuo in the dark over anhydrous silica gel. Yield was 240 mg, and the product was of sufficient purity to require no further treatment. The title compound was water-soluble but essentially insoluble in methanol, ethanol, and DMF. The IR spectrum was consistent for the indicated structure. Purity was indicated by homogeneity in the TLC n-butanol:acetic acid:water system, $R_f=0.78$, and in isopropanol-ammonia system, $R_f=0.80$.

Title complex possessed antitumor activity against the murine L1210 leukemia, vis-a-vis, $ID_{99.9}=29$ mg/kg, $LD_{50}=210$ mg/kg, Best%ILS=200, and figure of merit=14.

EXAMPLE 9

Preparation of 3-Ketoglutarato trans(−)-1,2-Diaminocyclohexane Platinum(II)

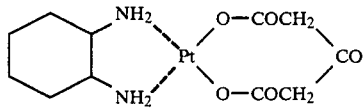

A mixture of cis-dichloro trans(−)-1,2-diaminocyclohexane platinum(II) (380 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. To the filtrate was added 3-ketoglutaric acid (160 mg), and the reaction mixture was stirred for 2 hours at 50° C. in the dark. The solution turned from light yellow to dark gold. Product was obtained by evaporation in vacuo. It was dried in vacuo in the dark over anhydrous silica gel. No further purification was required. The yield was 250 mg. The title complex was soluble in water and methanol, slightly soluble in ethanol, but insoluble in DMF. Its IR spectrum was compatible with the indicated structure. It was homogeneous as judged by TLC. In the n-butanol system the $R_f$ 0.75, while in the isopropanol, it was 0.70.

The antitumor activity of title complex against murine leukemia L1210 is indicated by $ID_{99.9}=22$ mg/kg, $LD_{50}=65$ mg/kg, Best%ILS=163, and figure of merit=5.

EXAMPLE 10

Synthesis of Ribose-5-Phosphato trans(−)-1,2-Diaminocyclohexane Platinum(II)

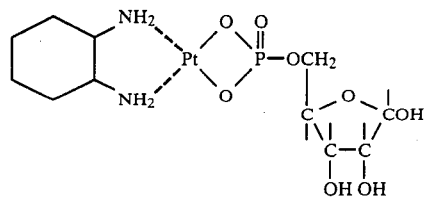

A mixture of cis-dichloro trans(−)-1,2-diaminocyclohexane platinum(II) (380 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. Ribose-5-phosphate (230 mg) was added to the filtrate, and the reaction mixture was stirred in the dark at 50° C. for 2 hours. Solution changed from yellow to colorless. Product was obtained by evaporation of the reaction mixture to dryness in vacuo; it was washed with methanol, and the product was dried in vacuo in the dark over anhydrous silica gel. No further purification was needed. The yield was 215 mg. The complex was readily soluble in water and D5W but insoluble in methanol and ethanol. IR spectrum was compatible with the structure shown above. Homogeneity of the complex was indicated by TLC in n-butanol system, R$_f$ of 0.75 and the isopropanol system, R$_f$ of 0.80.

The title compound possessed antitumor activity against leukemia L1210; its $ID_{99.9}=7$ mg/kg, $LD_{50}=22$ mg/kg, the Best%ILS=200, and the figure of merit=6.

EXAMPLE 11

Formation of 2-Aminoethylphosphato trans(−)-1,2-Diaminocyclohexane Platinum(II)

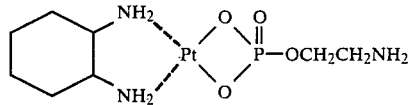

A mixture of cis-dichloro trans(−)-1,2-diaminocyclohexane platinum(II) (380 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. Phosphoethanolamine (150 mg) was mixed with the filtrate and stirred in the dark for 2 hours at 50° C. During this time the solution changed from yellow to green, and subsequently it was evaporated to dryness in vacuo. The product was dried in the dark in vacuo as usual. The yield was 185 mg, and the product was sufficiently pure to require no further treatment. The complex was soluble in water, methanol, and ethanol, but insoluble in acetone and DMF. Its IR spectrum was compatible with the formula shown above. Homogeneity was verified by TLC in the butanol system, $R_f=0.75$, and in the isopropanol system, $R_f=0.70$.

The title compound possessed antitumor activity against leukemia L1210. It had an $ID_{99.9}$ of 25 mg/kg, and $LD_{50}$ of 250 mg/kg, its Best%ILS was 200, and the figure of merit was 20.

EXAMPLE 12

Preparation of bis(Perfluorooctanoato) trans(−)-1,2-Diaminocyclohexane Platinum(II)

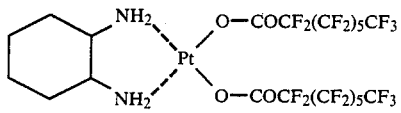

cis-Dichloro trans(−)-1,2-diaminocyclohexane platinum(II) (380 mg) and silver nitrate (340 mg) in 20 ml of water were stirred in the dark at room temperature for 24 hours. The reaction mixture was filtered to remove insoluble silver chloride. Perfluorooctanoic acid (828 mg) in 10 ml of water was treated with dilute sodium hydroxide solution to a pH of 5.5, and this was added to the filtrate mentioned above. The reaction mixture was stirred at 60° C. for 30 minutes. A white precipitate formed, and this was collected by filtration. It was washed with water and dried in vacuo in the dark as usual. Further purification was unnecessary. Yield corresponded to 300 mg. The title complex was slightly soluble in methanol and ethanol at room temperature but very soluble in hot ethanol. The product was essentially insoluble in water. IR spectroscopy was compatible with the structure shown above. Purity of the complex was indicated by TLC; the $R_f$ was 0.90 in the butanol system and 0.90 in the isopropanol system. The complex was dissolved in warm ethanol and added to an excess of intravenous lipid emulsion. Under these conditions, the title product was incorporated in the lipid micelles and, in this form, administered i.p. to L1210-bearing mice. Under these circumstances, the $ID_{99.9}=20$ mg/kg, the $LD_{50}=90$ mg/kg, the Best-%ILS=100, and the figure of merit was 5.

EXAMPLE 13

Synthesis of n-Hexylphosphonator trans(−)-1,2-Diaminocyclohexane Platinum(II)

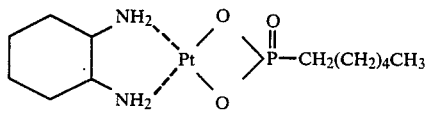

A mixture of cis-dichloro trans(−)-1,2-diaminocyclohexane platinum(II) (380 mg) and silver sulfate ($Ag_2SO_4$, 312 mg) in 25 ml water was stirred at room temperature in the dark for 24 hours. The resulting suspension was filtered (no silver was detectable in the filtrate), and barium hydroxide [$Ba(OH)_2.8H_2O$, 315 mg] was added to the filtrate and the stirring continued at room temperature in the dark for 24 hours. The reaction mixture was filtered to remove barium sulfate. n-Hexylphosphonic acid (203 mg) was added to the filtrate and stirred 30 minutes at 50° C. in the dark. A yellow precipitate separated and was collected by filtration. It was washed with water and dried as usual. No purification of this product was required. Its yield was 195 mg. The title complex was essentially insoluble in water, chloroform, dioxane, and butanone, slightly soluble in methanol and ethanol at room temperature, but quite soluble in warm ethanol. The IR spectrum was consistent with the structure shown above. Purity of the complex was indicated by TLC in the n-butanol system, $R_f=0.95$, and the isopropanol system, $R_f=0.95$.

The complex, dissolved in warm ethanol, was added to an excess of an intravenous lipid emulsion so as to incorporate it into the lipid micelles. It was administered in this form to $BDF_1$ mice bearing the L1210 tumor. It demonstrated an $ID_{99.9}=19$ mg/kg, and $LD_{50}=135$ mg/kg, an optimal percent ILS=150, and figure of merit=11.

EXAMPLE 14

Preparation of (Pyridoxal Phosphato) trans (−)-1,2-Diaminocyclohexane Platinum(II)

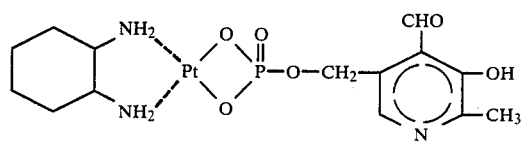

A mixture of cis-dichloro trans(−)-1,2-diaminocyclohexane platinum(II) (380 mg) and silver sulfate ($Ag_2SO_4$, 312 mg) in 25 ml water was stirred at room temperature in the dark for 24 hours. The resulting suspension was filtered (no silver was detected in the filtrate), and barium hydroxide [$Ba(OH)_2.8H_2O$, 315 mg[ was added to the filtrate and the stirring continued at room temperature in the dark for 24 hours. The reaction mixture was filtered to remove barium sulfate. To the filtrate was added pyridoxal phosphate (237 mg), and the mixture was stirred at 50° C. for 2 hours. The color of the solution changed from yellow to reddish brown. The reaction product was obtained by low temperature evaporation in vacuo, and the complex was dried in vacuo over anhydrous silica gel. The yield was 220 mg. The product required no further purification. The title complex was water-soluble. IR spectroscopy was compatible with the structure indicated above. Its homogeneity was determined by TLC; the $R_f$ in the butanol system was 0.80 and the $R_f$ in the isopropanol system was 0.70.

When tested against murine leukemia L1210, this complex demonstrated 140% ILS at a dose of 160 mg/kg, and 120% ILS at 100 mg/kg, 110% ILS at 40 mg/kg, and some indication of host toxicity at 200 mg/kg.

EXAMPLE 15

Synthesis of bis(Pentafluoropropionato) trans(−)-1,2-Diaminocyclohexane Platinum(II)

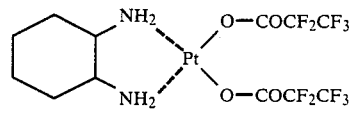

cis-dichloro trans(−)-1,2-diaminocyclohexane platinum(II) (380 mg) and silver sulfate (340 mg) in 20 ml water were stirred in the dark at room temperature for 24 hours. The reaction mixture was filtered to remove insoluble silver chloride. Pentafluoropropionic acid (656 mg) was suspended in 10 ml of water and treated with dilute sodium hydroxide solution to a pH of 5.5. This was then added to the filtrate of the reaction mixture described above. Stirring continued at 50° C. for 30 minutes. A white precipitate formed, and this was collected by filtration. It was washed with water and dried in vacuo in the dark over anhydrous silica gel. There was no need for further purification. Yield corresponded to 228 mg. The title complex was soluble in methanol and ethanol but insoluble in water. IR spectroscopy was compatible with the structure indicated. TLC in the n-butanol:acetic acid: water system gave an $R_f=0.85$ while in the isopropanol:0.1N ammonium hydroxide system, the $R_f$ was 0.95.

For testing against the murine L1210, this complex was dissolved in ethanol and incorporated into the lipid micelles of an i.v. lipid emulsoid. The results were as follows:

| Dose, mg/kg | % ILS |
|---|---|
| 120 | −30 |
| 90 | 40 |
| 60 | 40 |
| 40 | 97 |
| 30 | 143 |
| 10 | 40 |

EXAMPLE 16

Formation of 2-Hydroxyethane-1,1-Diphosphonato trans(−)-1,2-Diaminocyclohexane Platinum(II)

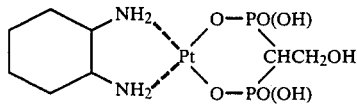

A mixture of cis-dichloro trans(−)-1,2-diaminocyclohexane platinum(II) (380 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. 2-Hydroxyethane-1,1-diphosphonic acid (200 mg) was added to the filtrate, and the mixture was stirred for 2 hours at 50° C. in the dark. The reaction mixture changed from light yellow to colorless. This platinum complex was obtained by low temperature evaporation in vacuo. The solid was washed with methanol and dried in vacuo in the dark as usual. No further purification was necessary. The yield was 200 mg. The product was soluble in water and in D5W but insoluble in methanol. IR spectrum was consistent with the structure shown above. In the n-butanol TLC system, the $R_f$ was 0.50 while in the isopropanol system, the $R_f$ was 0.80.

The title complex showed some antitumor activity against leukemia L1210 as follows: 110%ILS at a dose of 160 mg/kg and 60%ILS at a dose of 40 mg/kg.

EXAMPLE 17

Synthesis of Arsonoacetato trans(−)-1,2-Diaminocyclohexane Platinum(II)

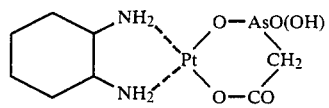

cis-Dichloro trans(−)-1,2-diaminocyclohexane platinum(II) (380 mg) was mixed with 398 mg of disilver arsonoacetic acid and the mixture stirred in the dark for 24 hours at room temperature. The mixture was filtered, and the filtrate was evaporated to dryness at low temperature in vacuo. The product was washed with methanol and dried in vacuo as usual. No further purification was required; the yield of the final product was 195 mg. The complex was soluble in water and in D5W but insoluble in methanol. Its IR spectrum was consistent with the formula given above. In the n-butanol TLC system, this product had an $R_f$ of 0.62 while in the isopropanol system, its $R_f$ was 0.51.

Against L1210, the title product demonstrated:

| Dose mg/kg | % ILS |
|---|---|
| 60 | 136 |
| 40 | 130 |
| 10 | 80 |
| 6 | 109 |

EXAMPLE 18

Synthesis of Phosphonoacetato 1,2-Diamino-2,4-Dimethylpentane Platinum(II)

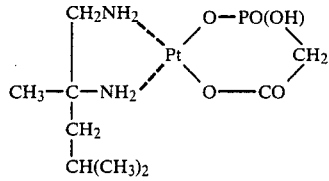

A mixture of cis-dichloro 1,2-diamino-2,4-dimethylpentane platinum(II) (395 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. To the filtrate was added 140 mg of phosphonoacetic acid, and the reaction mixture was stirred and heated 1.5 hours at 50° C. The mixture changed from yellow to colorless. Isolation of the product was achieved by low temperature evaporation in vacuo, and the resulting product was leached with methanol. It was dried in the dark in vacuo as usual. No further purification was required. The yield was 169 mg. The complex was soluble in water but insoluble in methanol. Its IR spectrum was that to be expected from the structure indicated above. It was homogeneous according to TLC; in the n-butanol system, the $R_f$ was 0.75 and in the isopropanol system, the $R_f$ was 0.50.

When the title complex was evaluated for antitumor activity in the L1210 system, results were as follows:

| Dose mg/kg | % ILS |
| --- | --- |
| 140 | 63 |
| 70 | 117 |
| 40 | 100 |
| 10 | 100 |
| 2.5 | 40 |

EXAMPLE 19

Preparation of Phosphonoacetato 3,4-Diamino-2,5-Dimethylhexane Platinum (II)

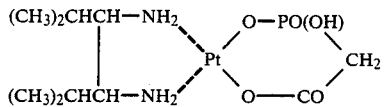

A mixture of cis-dichloro 3,4-diamino-2,5-dimethylhexane platinum(II) (410 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. To the filtrate phosphonoacetic acid (140 mg) was added, and the reaction was stirred at 50° C. for 2 hours. The mixture turned from yellow to colorless. The complex was obtained upon evaporation to dryness at low temperature in vacuo, and it was washed with methanol. Drying in vacuo in the dark was achieved as usual. There was no need for further purification. The yield was 235 mg. The complex was soluble in water but insoluble in methanol. The IR spectrum was consistent with the formula above. TLC in the butanol system showed an R$_f$ of 0.69 and in the isopropanol system of 0.72.

When evaluated in the leukemia L1210 system, this complex showed 103%ILS at a dose of 40 mg/kg and 30%ILS at a dose of 10 mg/kg.

EXAMPLE 20

Synthesis of Phosphonoacetato trans-1,2-Diaminocyclooctane Platinum(II)

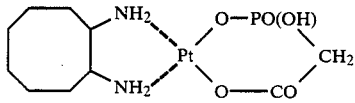

A mixture of cis-dichloro trans-1,2-diaminocyclooctane platinum(II) (408 mg) and silver sulfate (Ag$_2$SO$_4$, 312 mg) in 25 ml water was stirred at room temperature in the dark for 24 hours. The resulting suspension was filtered (no silver was detectable in the filtrate), and barium hydroxide [Ba(OH)$_2$.8H$_2$O, 315 mg] was added to the filtrate and the stirring continued at room temperature in the dark for 24 hours. The reaction mixture was filtered to remove barium sulfate. To the filtrate was added phosphonoacetic acid (140 mg), and the reaction mixture was stirred and heated 2 hours at 50° C. in the dark. During this time the reaction mixture changed from light yellow to colorless. The complex was obtained by evaporation to dryness at low temperature in vacuo, and it was washed with methanol prior to drying in vacuo over anhydrous silica gel. No further purification was necessary. The yield was 250 mg. The complex was soluble in water but essentially insoluble in methanol. The IR spectrum was compatible with the formula shown above. Purity of the complex was indicated by homogeneity in the n-butanol TLC system, R$_f$=0.72, and the isopropanol system, R$_f$=0.65.

Antitumor activity against L1210 was as follows:

| Dose mg/kg | % ILS |
| --- | --- |
| 160 | 67 |
| 40 | 143 |
| 10 | 33 |

EXAMPLE 21

Synthesis of bis(Heptafluorobutyrato) 1-Aminomethylcyclooctylamine Platinum(II)

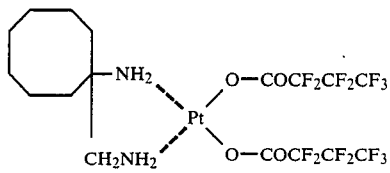

cis-Dichloro 1-aminomethylcyclooctylamine platinum(II) (422 mg) and silver sulfate (340 mg) in 20 ml of water were stirred in the dark at room temperature for 24 hours. The reaction mixture was filtered. Heptafluorobutyric acid (856 mg) was suspended in 10 ml water and treated with dilute sodium hydroxide to a pH of 5.5. This was then added to the filtrate described above, and the reaction mixture was stirred at 50° C. for 2 hours. A white precipitate formed and was collected by filtration. It was washed with water and dried in vacuo in the dark over anhydrous silica gel. No further purification was required. The yield was 210 mg. The complex was soluble in methanol and in ethanol but insoluble in water. IR spectroscopy was consistent with the formula above. Purity of the complex was indicated by an R$_f$ of 0.95 in the butanol TLC system and of 0.95 in the isopropanol system as well.

When tested in the L1210 system, this platinum complex demonstrated an ID$_{99.9}$ of 5 mg/kg, an LD$_{50}$ of 130 mg/kg, a Best%ILS of 165, and figure of merit of 43.

We claim:

1. A compound of the formula

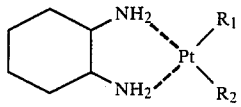

wherein the stereoisomerism of 1,2-diaminocyclohexane is cis-, trans(+)-, or trans(−)-, and R$_1$ and R$_2$ are both

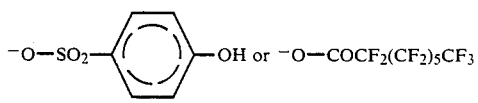

or $R_1$ and $R_2$ when taken together represent a group of the formula

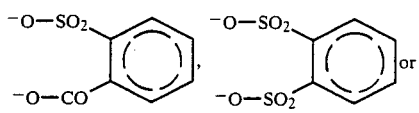

2. A compound of claim 1 wherein $R_1$ and $R_2$ are both 4-hydroxyphenylsulfonato, said compound having the formula

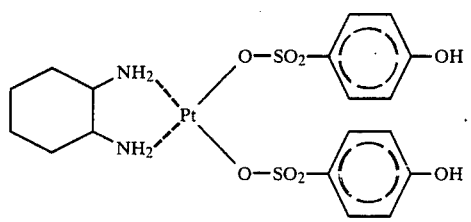

3. A compound of claim 1 wherein $R_1$ and $R_2$ are both perfluorooctanoato, said compound having the formula

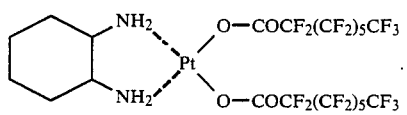

4. A compound of claim 1 wherein $R_1$ and $R_2$ when taken together represent 2-sulfobenzoato, said compound having the formula

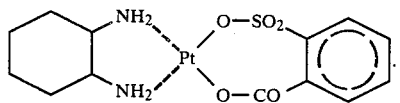

5. A compound of claim 1 wherein $R_1$ and $R_2$ when taken together represent 1,2-benzenedisulfonato, said compound having the formula

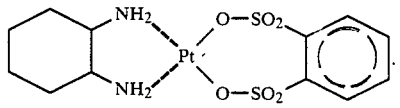

6. A compound of claim 1 wherein $R_1$ and $R_2$ when taken together represent 3-ketoglutarato, said compound having the formula

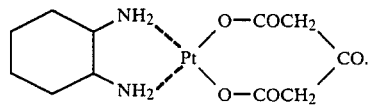

7. A compound of the formula

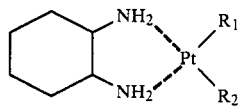

wherein the stereoisomerism of 1,2-diaminocyclohexane is trans(—) and $R_1$ and $R_2$ are both

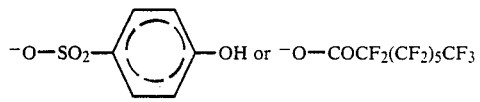

or wherein $R_1$ and $R_2$ when taken together represent a group of the type

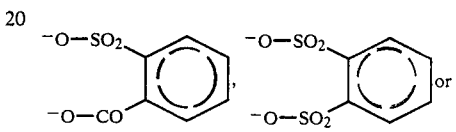

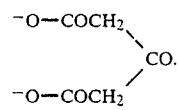

8. A compound of claim 7 wherein $R_1$ and $R_2$ are both 4-hydroxyphenylsulfonato said compound having the formula

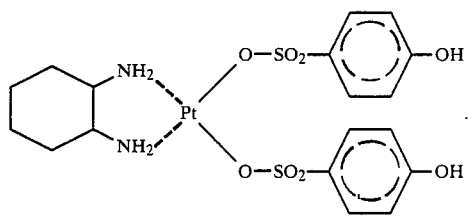

9. A compound of claim 7 wherein $R_1$ and $R_2$ are both perfluorooctanoato, said compound having the formula

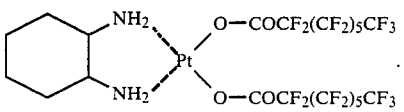

10. A compound of claim 7 wherein $R_1$ and $R_2$ when taken together represent 2-sulfobenzoato, said compound having the formula

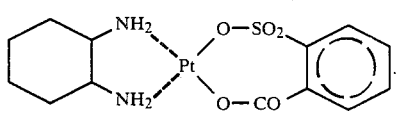

11. A compound of claim 7 wherein $R_1$ and $R_2$ when taken together represent 1,2-benzenedisulfonato, said compound having the formula

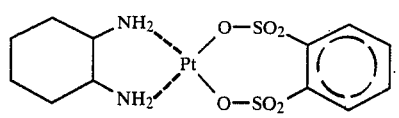
12. A compound of claim 7 wherein $R_1$ and $R_2$ when taken together represent 3-ketoglutarato, said compound having the formula
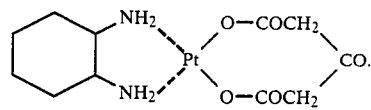
* * * * *